United States Patent [19]
van Oostrom et al.

[11] Patent Number: 6,074,345
[45] Date of Patent: Jun. 13, 2000

[54] PATIENT DATA ACQUISITION AND CONTROL SYSTEM

[75] Inventors: Johannes H. van Oostrom; Richard J. Melker, both of Gainesville, Fla.

[73] Assignee: University of Florida, Gainesville, Fla.

[21] Appl. No.: 09/179,768

[22] Filed: Oct. 27, 1998

[51] Int. Cl.[7] .................................................. A61B 5/00
[52] U.S. Cl. ........................ 600/300; 128/904; 128/920
[58] Field of Search .................................. 600/300, 301, 600/341; 128/903, 904, 920; 604/226, 265, 403; 210/782; 428/411.1, 500; 395/200.3; 702/19, 85, 105

[56] References Cited

U.S. PATENT DOCUMENTS

| | | | |
|---|---|---|---|
| 4,838,275 | 6/1989 | Lee | 128/670 |
| 5,060,140 | 10/1991 | Brown et al. | 364/200 |
| 5,400,246 | 3/1995 | Wilson et al. | 364/146 |
| 5,467,773 | 11/1995 | Berglson et al. | 128/709 |
| 5,509,121 | 4/1996 | Nakata et al. | 395/200.1 |
| 5,535,375 | 7/1996 | Eshel et al. | 391/500 |
| 5,544,649 | 8/1996 | David et al. | 128/630 |
| 5,553,609 | 9/1996 | Chen et al. | 128/630 |
| 5,558,638 | 9/1996 | Evers et al. | 604/66 |
| 5,586,305 | 12/1996 | Eidson et al. | 395/500 |
| 5,590,648 | 1/1997 | Mitchell et al. | 128/630 |
| 5,632,022 | 5/1997 | Warren et al. | 395/350 |
| 5,694,546 | 12/1997 | Reisman | 395/200.9 |
| 5,748,612 | 5/1998 | Stoevhase et al. | 370/230 |
| 5,776,057 | 7/1998 | Swenson et al. | 600/301 |
| 5,974,237 | 10/1999 | Shurmer et al. | 395/200.54 |

*Primary Examiner*—Eric F. Winakur
*Assistant Examiner*—Charles Marmor, II
*Attorney, Agent, or Firm*—Saliwanchik, Lloyd & Saliwanchik

[57] ABSTRACT

The present invention solves this communication problem by providing a method and apparatus for connecting to and coordinating data communications of various medical devices having different communication protocols. In a preferred embodiment, the invention provides a way to recognize common parameters and separate out only that part of the communication that is different between and specific to the various monitors and therapeutic devices. The invention efficiently utilizes defined common parameters for protocol types and selectively configures the specific settings when required, automatically.

38 Claims, 15 Drawing Sheets

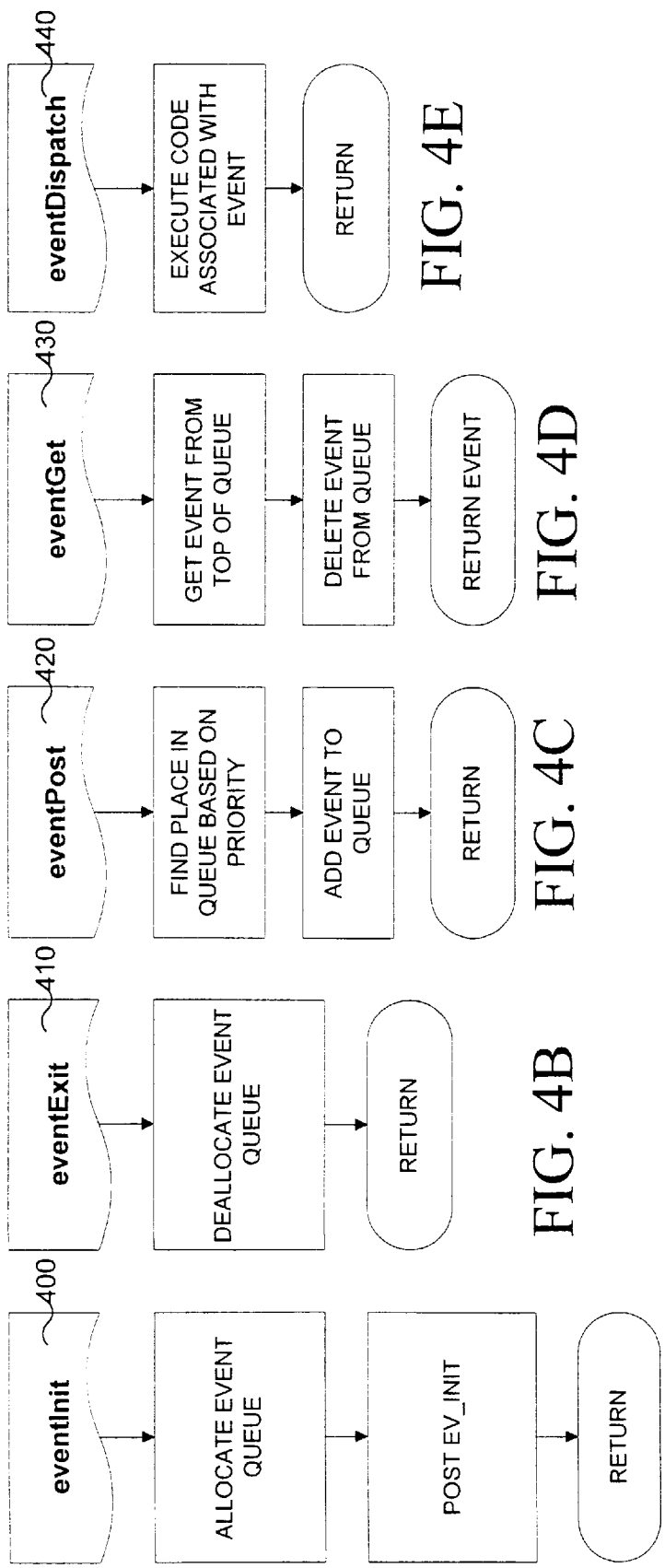

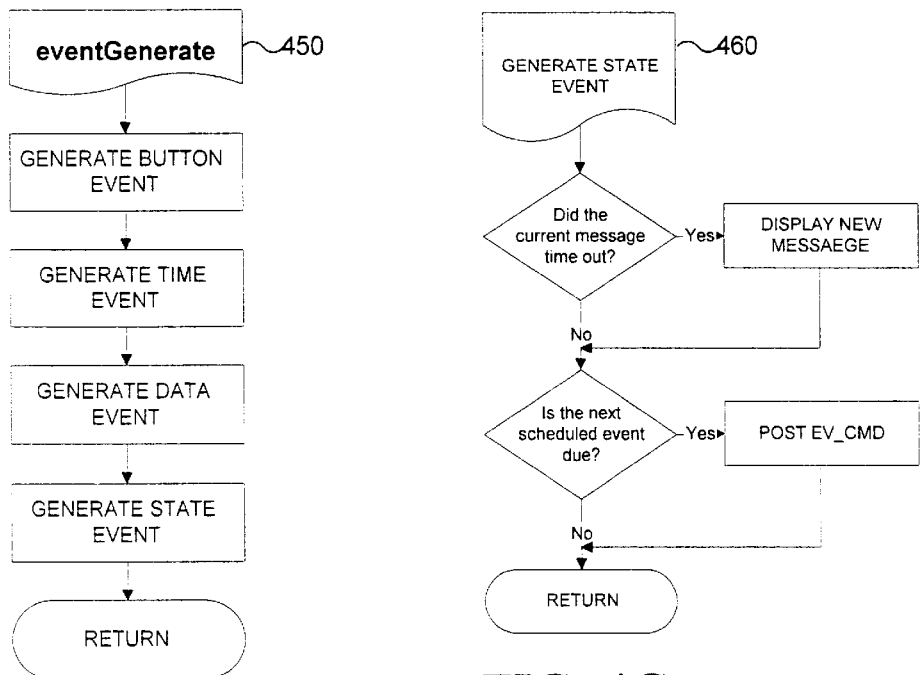
FIG. 4F
FIG. 4G
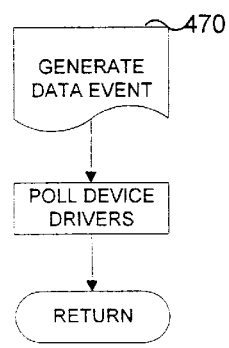
FIG. 4H
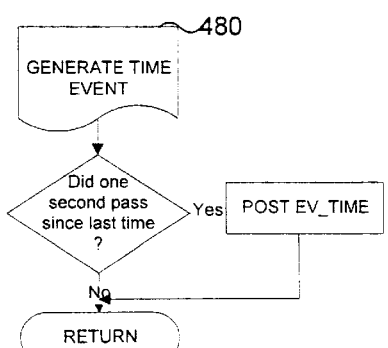
FIG. 4I
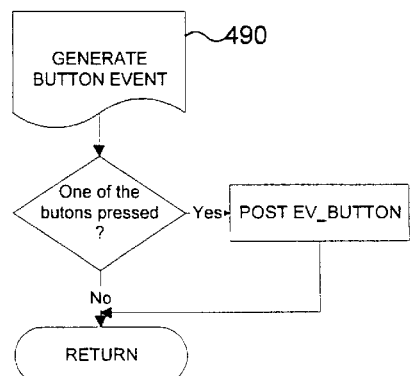
FIG. 4J

PATIENT DATA ACQUISITION AND CONTROL SYSTEM

FIELD OF THE INVENTION

This invention generally pertains to communications between medical devices and, more specifically, pertains to a method and apparatus for connecting to and coordinating data communications of various medical devices having different communication protocols.

BACKGROUND OF THE INVENTION

Medical monitoring devices are used extensively in hospitals, clinics, alternative site care, i.e., nursing homes, and at home to monitor a variety of medical conditions. These devices basically measure a physiologic condition/state/value from a patient and report the data representative thereof as an output of the device, typically by displaying the data on a display of the monitoring device. For example, when a measurement has been completed by a non-invasive blood pressure monitor, the systolic, diastolic, and mean blood pressure as well as the heart rate are displayed on the monitoring device. Such information could also be recorded manually by the patient or a health care provider or possibly stored in the device for future display.

Medical treatment/therapeutic devices are also used extensively in health care. These devices typically deliver a therapeutic treatment to a patient as part of the medical treatment. Examples are infusion pumps (delivering fluids and/or drugs to the patient), and ventilators (delivering gas to the patient). Each therapeutic device has a number of settings that can be modified. This is typically accomplished by various input peripherals such as buttons, knobs, key pads, and the like on the therapeutic device.

With the rapid development of computer technology, such medical devices are now mainly microprocessor-based. This technology now allows for the addition of external communications features (input/output) on the devices. At first, this communication was geared toward technicians to service the device and sometimes use the device to print out tables of data. Over the last 5 years, however, there has been a move to using this communication feature to report the output data measured by a monitor to another location (often a central office) and to remotely modify settings on a therapeutic device by communicating the appropriate input information.

A direct connection between a single device (monitor or therapeutic device) and a central station can be readily constructed. However, a problem arises in coordinating data and transmissions when multiple monitors and/or therapeutic devices are used simultaneously or interchangeably (especially if such devices were not designed to work together or come from different manufacturers). This is because medical monitoring devices and therapeutic devices differ in at least three aspects: 1) their hardware communication protocol, 2) their software communication protocol, and 3) their data (input and/or output).

In a number of industries, this problem is solved by agreeing on a set of standards to enable computers and devices to connect with one another and to exchange information with as little error as possible (i.e., standardized hardware and software communication protocols and data formats). Some of the known protocols include, for example, OSI (Open Systems Interconnection) and SNA (Systems Network Architecture). There are a multitude of standards affecting different aspects of communication, such as file transfer (XMODEM, ZMODEM), handshaking (XON/XOFF), and network transmissions (CSMA/CD).

To date, unfortunately, no standards have been developed that govern the communication process and protocols for medical devices. As a result, the data that is communicated is non-standardized, differs from manufacturer to manufacturer and even sometimes differs with various software versions of the same device. In addition, configuration data needed to start the communication process is also non-standardized.

For example, a certain hardware protocol for serial connections (e.g., RS-232, RS-422/423/449, etc.) may be defined by a number of communication parameters (e.g., baud rate, data bits, stop bits and parity). Each of the parameters have a number of settings (e.g., baud rates of 300, 600, 1200, 2400, 9600, 19200, 38400, 57600, 115200, etc.) which have not been standardized between devices. Devices also have different software communication protocols which define various formatting of data, such as if the data is designed for a line printer versus packetized data. The format is generally the structure or appearance of a unit of data. For line printers, there are parameters defining end of line characters and formats for the line. In packetized data, for example, there are parameters defining formats (packet, data), headers, and end of packet information. Again, each of these parameters include a variety of settings which are not standard in the industry. That is, none of the settings for the above-noted parameters have been standardized. Therefore, for each device, the setting information for each parameter must be determined and configured. This process is tedious and time consuming. It requires a great deal of repetition and additional software and consumes more resources such as RAM, CPU time, coding, and the like. To avoid this problem, many choose to restrict their choice of devices to the same manufacturer where the parameter settings are hopefully the same. However, this does not provide a solution to the problem, since certain manufacturers do not sell all of the devices which may be necessary or do not provide a desired device with certain features.

Consequently, a need arises for providing a way to efficiently connect to these various devices, regardless of manufacturer and/or communication protocol parameter settings.

BRIEF SUMMARY OF THE INVENTION

The present invention provides a unique method and apparatus for connecting to and coordinating data communications of various devices of differing protocols and parameter settings. In a preferred embodiment, the invention provides a way to recognize common parameters of a protocol type and separate out only that part of the communication that is different between and specific to the various monitors and therapeutic devices. The invention efficiently utilizes defined common parameters of a protocol and selectively configures the specific parameter settings when required, automatically.

Specifically, in a preferred embodiment of the invention, a method of communicating with various medical devices is provided which includes, for each connected device, identifying the common parameters for a specific protocol type and automatically configuring settings for said specific parameters. The common parameters are substantially standard between various devices having the same protocol type. For example, the common parameters for the RS-232 hardware protocol type are baud rate, data bits, stop bits, and parity. Within each of these parameters, there are specific settings which vary from device to device (e.g., baud rates of 300, 600, 1200, 2400, 9600, 19200, 38400, 57600, 115200, etc.). The specific settings for each connected device are substantially non-standard between various devices.

In a preferred embodiment, the specific parameter settings are automatically configured for each device by generally polling each connected device, comparing response from the polling step to a list of specific responses for each device, and setting the specific parameter settings for each device based on the comparison. This can be accomplished by sending a specific request string on a port for a device in a list of devices, and if a response to the request string is matched identifying a specific device, configuring settings for the common parameters associated with the protocols for the device on the port, otherwise repeat sending request strings for next device in the list until a match. Preferably, a proper baud rate setting is set for the device prior to sending the request string and the steps are repeated for each port.

In an alternate embodiment, the specific parameter settings are automatically configured for each device by a) selecting a baud rate setting out of a list of standard baud rate settings, b) sending a first request string on a port, and if a first response to the first request string is matched, c) configuring settings for the common parameters associated with the protocols for a device which corresponds to the first response, otherwise repeat steps a through c for the next baud rate in the list of standard baud rates. If no responses are matched in the previous steps a through c, this embodiment may further include the steps of a) selecting a baud rate setting out of the list of standard baud rate settings, b) sending a second request string on a port, and c) if a second response to the second request string is matched, configuring settings for the common parameters associated with the protocols for a device which corresponds to the second response, otherwise repeat steps a through c herein for the next baud rate setting in the list of standard baud rate settings. Preferably, the steps are repeated for each port.

The present invention, in a preferred embodiment, also includes a system for communicating with various medical devices. This system includes, for each connected device, a routine for identifying the common parameters for a specific protocol type and a routine for automatically configuring settings for said specific parameters.

The present invention also provides a method and system for monitoring of at least one physiologic condition of at least one patient by: a) configuring a protocol of communication between at least one medical device and a data acquisition unit connected to at least one of the devices by identifying the common parameters for a specific protocol type and automatically configuring settings for said specific parameters; b) monitoring a patient's physiologic condition through at least one connected medical device to provide data representative of the physiologic condition; and c) communicating the data to the data acquisition unit connected to the device. The method may further include the step of storing the data in the data acquisition unit and transmitting the parameter to a remote location. The medical devices could include monitoring devices and/or therapeutic devices. If some form of therapeutic devices are used, or medical devices which can be adjusted with commands, the method may further include communicating a command to control the medical device through the data acquisition unit. The communication may be initiated at a location remote from the data acquisition unit. In this method, the specific parameter settings are automatically configured for each device by polling each connected device, comparing response from the polling step to a list of specific responses for each device, and selecting the specific parameter setting for each device based on the comparison.

BRIEF DESCRIPTION OF THE DRAWINGS

FIGS. 4a, 4b, 4c, 4d, 4e, 4f, 4g, 4h, 4i, and 4j are software flow diagrams of the functions and operation of the event system routines: initialization, exit, post, get from queue, dispatch, event generate, generate state, generate data, generate time, generate button routines respectively, of the present invention.

DETAILED DISCLOSURE OF THE INVENTION

Figure 1:
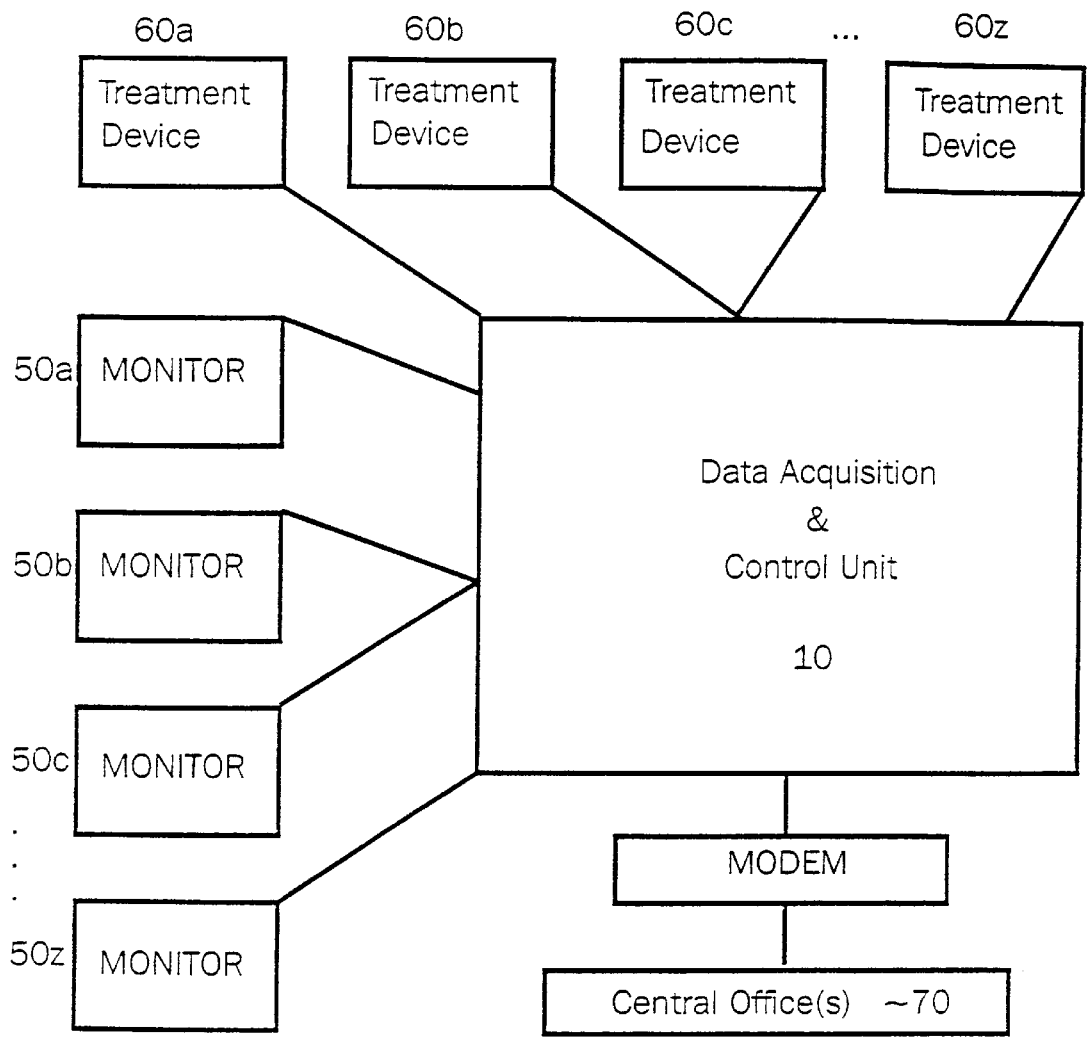
FIG. 1 is a block diagram of various monitors and therapeutic devices connected to the data acquisition and control unit of the present invention which may then be remotely connected to a central office or care center for reporting and storing data and controlling the attached devices.

FIG. 1 is a block diagram of various monitors 50a, 50b, . . . 50z and therapeutic devices 60a, 60b, . . . 60z connected to the data acquisition and control unit 10 of the present invention. The unit 10 is designed to recognize, understand, and communicate with each of these devices and their unique hardware communication protocol, software communication protocol, and data requirements (input and/or output).

Initially, in formulating a solution to the communication protocol problem between various medical devices, studies were made of several physiologic monitors and therapeutic devices available in the Department of Anesthesiology at the University of Florida. The goal of this study was to determine similarities and differences between the communication of these devices. The studies showed that the low-level hardware to communicate for most of the devices was the same, and conform to the EIA RS-232 standard (EIA 1988). [EIA Standard RS-232-C 1981 Electronic Industries Association Engineering Dept. EIA Standard RS-232-C: Interface between Data Terminal Equipment and Data Communication Equipment employing Serial Binary Data Interchange. Washington D.C., 1981.] However the data sent over this hardware connection and the settings and configuration of the connection are different for all monitors and therapeutic devices.

The other commonality that was discovered was the information/data sent or received over the connection. For example, a blood pressure monitor always sends systolic and diastolic blood pressure in mmHg, and a heart rate in beats/min. Based on this information, the present invention defined a common data/protocol format which would allow all of the information that comes from the monitor and all the information that goes to a therapeutic device to be in compliance.

Generally, the present invention solved the communication problem by providing a way to separate out only that part of the communication that is different between the various monitors and therapeutic devices, and to use common methods for the rest. Communicating with devices generally requires both hardware protocols (input/output ports, serial interface, RS-232, RS-422, parallel interface, DIN, SCSI, network interface, etc.) and software/data protocols (output stream format for display or printer, character printer format, line printer format, packetized format, etc.). Each of these protocols requires a certain set of parameters to define the protocol. For example, the RS-232 hardware port has the following parameters for communication: baud rate, data bits, stop bits, and parity. Each of these parameters, in turn, have specific settings (e.g., baud rate=300, 600, 1200, 2400, 9600, 19200, 38400, 57600, 115200, etc.) which are often unique to the device since no standardized settings have been established.

Although data values transmitted are often the same between similar types of devices (e.g., non-invasive blood pressure monitors generally transmit the following three data values: systolic value, diastolic value, and heart rate), the way that the data is transmitted varies from device to device. The way data is transmitted is accomplished by a certain defined protocol for communication. For example, the data can be transmitted in line printer format (protocol) or packetized format (protocol). If the protocol is of the line printer type, the parameters to define such type include the following: end of line character, format of the line. For each of these parameters, there is a particular setting such as "end of line character"="carriage return."

The present invention provides a unique method and apparatus for connecting to and coordinating data communications of various devices having different parameter settings. As used herein, the term "protocol" generally refers to both hardware protocols and software protocols used for communication between devices, systems, and the like. The term "parameter" refers to a constant in a particular protocol which varies in other protocols of the same type used to define the particular protocol. The term "setting" refers to the value assigned to a specific parameter. The term "data" refers to the actual information transmitted (medical sensor values, etc.) as opposed to the settings information.

Table 1 below shows the relationship between the hardware communication protocol, software communication protocol, and data requirements (input and/or output) for monitors/therapeutic devices with respect to the parameters and settings.

TABLE 1

| | Monitors/Therapeutic Devices | |
| --- | --- | --- |
| Aspects | Protocol | Parameter(settings) |
| Hardware Communication Protocol | RS232 | baud rate (#) data bits (#) stop bits (#) parity (even, odd, none) |
| | Other | par-1 (#) par-2 (#) par-3 (#) par-n (#) |
| Software Communication Protocol | Line Printer | EOL (char) format (data) |
| | Packetized | packet format (type) header (data length) data (# bytes) EOP (CRC field) |
| Data Type | Type 1 - Blood Pressure | systolic BP (#) diastolic BP (#) heart rate (#) SpO2 (#) |
| | Type 2 - Infusion Pump | par-1 (#) (e.g., flow rater) par-2 (#) (e.g., concentration) par-n (#) (e.g., drug name) |
| | Type 3 - Other | par-1 (#) par-2 (#) |

For example, in the case of a simple blood pressure monitor that automatically sends data each time a new measurement has been taken, the present invention uses common methods to access the RS-232 hardware, common methods to store, forward, and/or analyze the information from the monitor, and uses specific methods to interpret the data stream from the monitor.

The common identified parameters for blood pressure monitors are generally the RS-232 hardware protocol and the data transmitted with the protocol. The RS-232 protocol defines voltages and timing sequences needed to communicate data. The same set of parameters are used to fully define a connection, namely, baud rate, number of data bits, number of stop bits, and parity. Settings for these parameters are specific to a particular device, but typically the following settings are available: baud rate=300, 600, 1200, 2400, 9600, 19200, 38400, 57600, or 115200; data bits=7 or 8; stop bits=0 or 1; parity=even, odd, or none. The set of data values transmitted with the protocol is also common between the same types of devices. For example, a non-invasive blood pressure monitor will usually transmit the following set of data: systolic value, diastolic value, and heart rate. These numeric values can be stored as an ASCII string or a binary representation like the IEEE float 754 specification. A timestamp can optionally be attached to the data.

The way this data is transmitted (the protocol) is different between devices (specific to the device). Two general formats are used: ASCII string terminated with a carriage return or a line feed (line printer format); or packetized protocol where binary data packets are sent back and forth. When the ASCII string format is used, the data and timestamp are also represented as ASCII. When a binary (packetized) format is used, the numeric data and timestamp data can be either ASCII or binary. When a packetized format is used, the following data items are usually present (their format depends on the device): header information (includes packet length, checksum, etc.), the data block (containing the numeric data, timestamp, units, etc.), end of packet information (usually contains a specific packet termination). Checksums are commonly calculated with the 16-bit CCITT checksum.

From the above-noted example, it can be seen that for almost any blood pressure monitor, the common parameters would be the RS-232 parameters of baud rate, number of data bits, number of stop bits, and parity (the setting for which are specific) and the set of data: systolic value, diastolic value, and heart rate (the format for which is specific). The software coding for these commonalities can be reused and only the specifics would need additional coding. Accordingly, when new blood pressure devices are added, the previously developed code for the above-identified common parameters can be re-used which saves time, resources, coding and the like.

To implement the present invention, first, a functional specification of the hardware was made. This particular implementation of the invention was designed to 1) communicate with several different physiologic monitors or therapeutic devices via a serial connection (RS-232), including sending commands to start measuring a parameter and collecting the parameters and waveform data from the device; 2) communicate via modem(or other communication device) with a central station 70 at certain (configurable) intervals, including accepting orders to monitor certain parameters at certain times from the central station and security -user/device identification; 3) display simple instructions to the patient; 4) accept simple input (button presses) from the patient; 5) provide an audio alarm to alert the patient to messages on the display or to indicate the next measurement is due; and 6) store data when there is no dial-up connection, even when there is a power failure.

Figure 2:
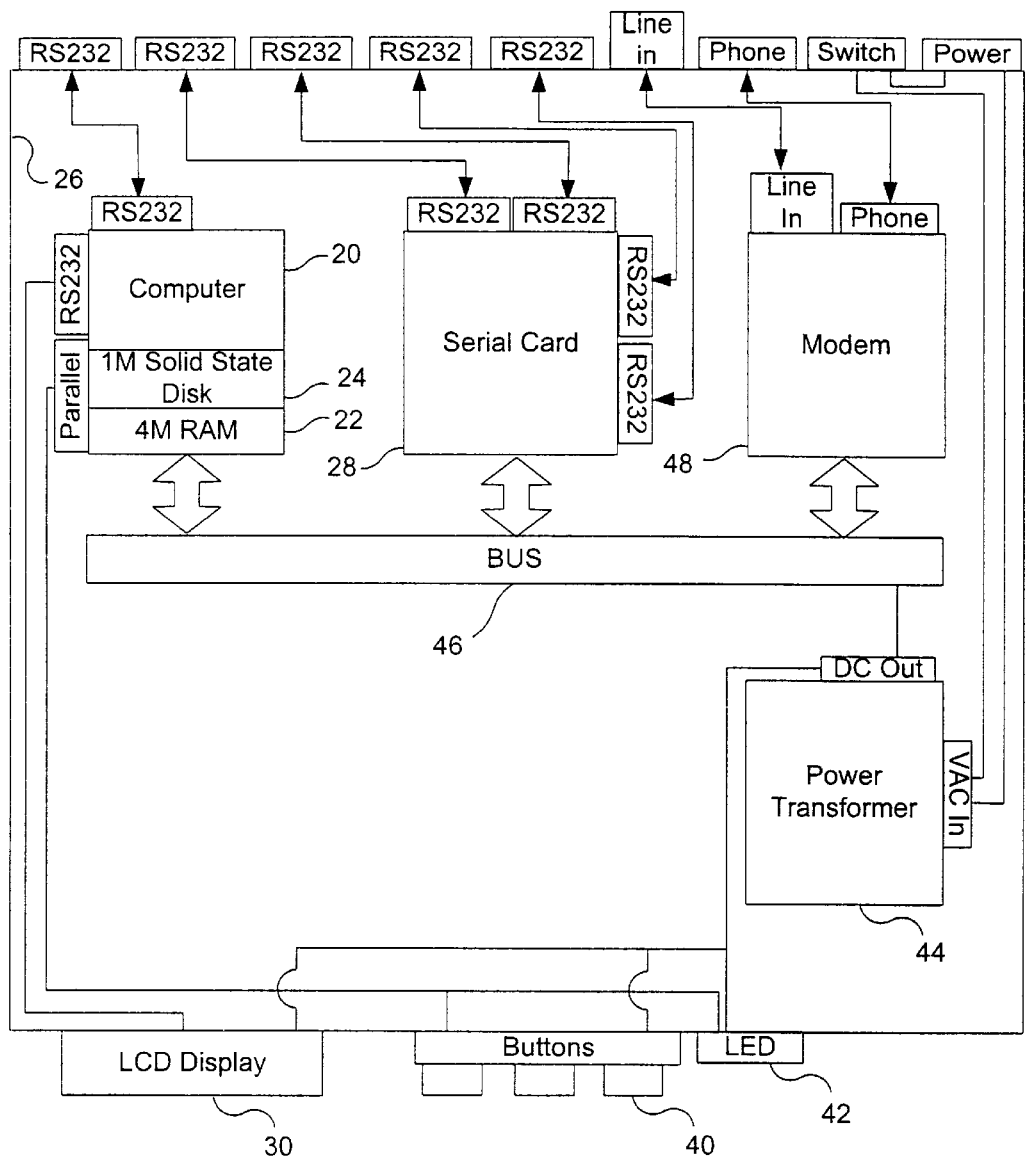
FIG. 2 is a schematic diagram of the circuitry of the data acquisition and control unit of the present invention.
Figure 3:
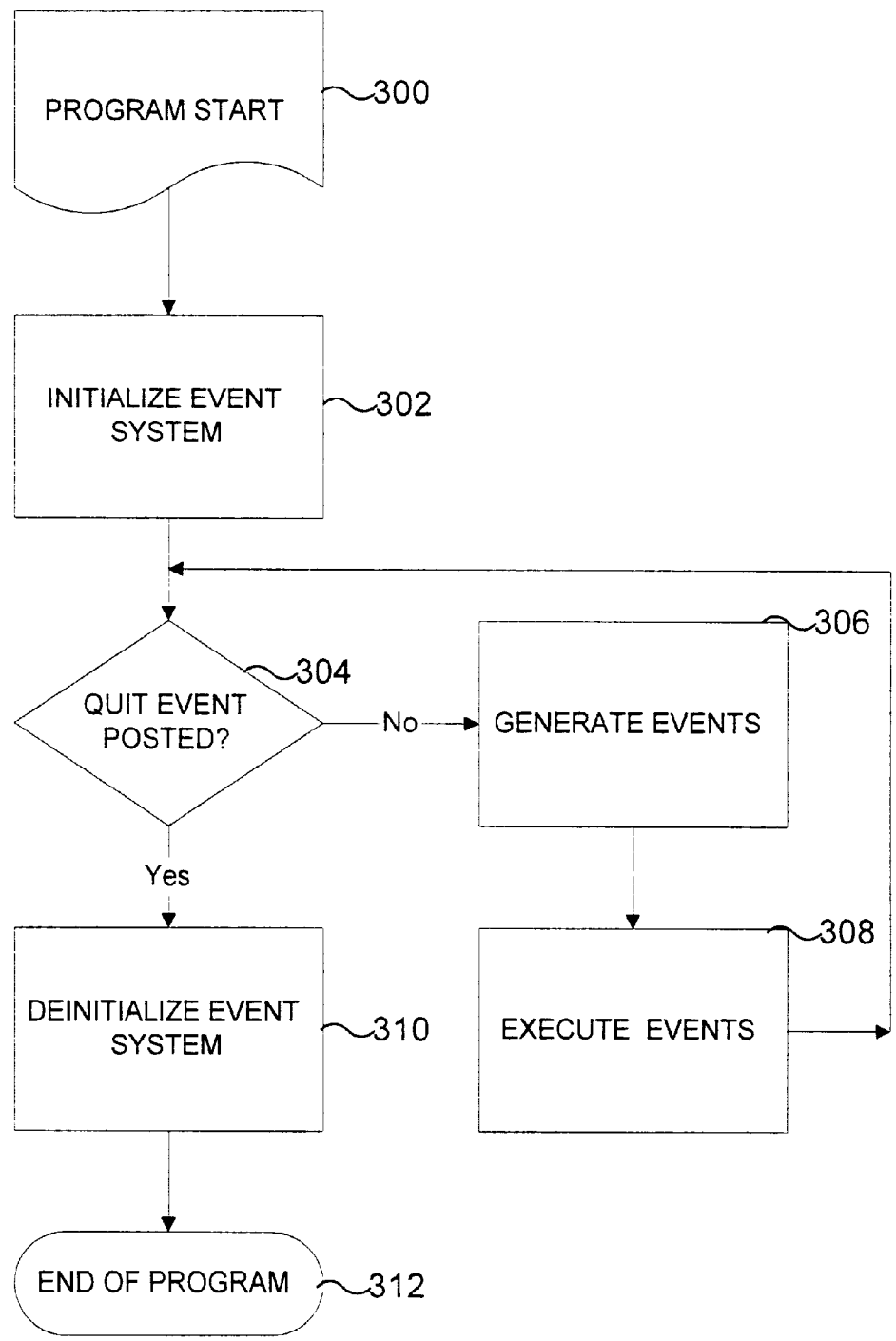
FIG. 3 is a software flow diagram of the functions and operation of the main program which generates events for data acquisition and control of the present invention.

As shown in FIG. 2, the preferred embodiment of the data acquisition and control unit 10 contains the following basic hardware elements: a microprocessor 20 for control (e.g., 386 SZ 40Mhz ISA card part # PC-310-386X, available from E.G. Technology Corp., Livingston, N.J., USA); semiconductor-based memory 22 (e.g., 4Mb memory part #MM1X36-70, available from E.G. Technology Corp.); a solid-state disk drive 24 for mass storage (e.g., 1.5Mb solid-state disk for PC-310 part #OT-SSD1.5MB, available from E.G. Technology Corp.); a backplane 26 with a plurality of slots (e.g., Backplane ISA 3 slot part #BP-13 available from E.G. Technology Corp.); a multi-port serial board 28 (e.g., four port serial board 16550 UARTS part #9013-S5-4, available from Byte Runner Technologies, Knoxville, Tenn., USA); and a display 30 (e.g., LCD backpack part # BPK-420L, available from Scott Edwards Electronics, Sierra Vista, Ariz., USA). A user interface 40 may include any standard input device(s) such as touch screen, push buttons, key board, mouse, and the like. A status light 42 may also be included. Power is preferably provided by a power source, not shown, which may be alternating or direct current (battery operated) or include battery back-up power. Standard 115 VAC power may be utilized with a power transformer 44 to provide the necessary DC output for the circuitry. A standard bus configuration 46 transmits data between the microprocessor, memory, ports and modem. If external communication is desired, a modem 48 or similar external communication device (telephone, microwave relay, satellite link, cable, network, and the like), may be provided.

The unit 10 may be directly or remotely connected to a central office 70 or care center for reporting and storing data and controlling the attached devices. In a preferred embodiment, the data acquisition and control unit 10 of the present invention preferably utilizes a single board computer capable of running the MS-DOS operating system. It is envisioned that the remote unit may be used in a variety of situations where remote monitoring may become necessary, such as on vessels out at sea, rural villages and towns, and the like. The data may be transmitted (via modem, satellite, radio wave, wiring, infra-red, or other communication means) to a "central station" or other location as desired, such as a doctor's office, nurse's station, third-party monitoring station, alternative sites, base stations, port/naval stations (from a ship), and the like. The term "remote" as used herein does not necessarily mean "far removed." The unit 10 may be directly attached (hard-wired) to its "central office" in the same room or building. Furthermore, the functions of the "central office" (such as visual displays, data recording, control, etc.) may be incorporated into a single system in conjunction with the unit 10 if desired.

The method of the present invention in a preferred embodiment can be implemented in "C" programming language with the program running on an MS-DOS operating system. The method of the present invention is described with reference to the following description and flow diagrams of FIGS. 3–12.

The main loop of the software (FIG. 3) is operating an event system in which each task is given a finite amount of processor time. The main program 300 starts with an INITIALIZE EVENT SYSTEM 302 (the details of which are shown in FIG. 4a, evenInit function 400). The event system contains an event queue that allows prioritization and execution of events. The program checks for a QUIT EVENT 304 and if not posted proceeds to GENERATE EVENTS 306 and EXECUTE EVENTS 308. This loop continues until a QUIT EVENT is posted and proceeds to DEINITIALIZE EVENT SYSTEM 310 to the end of the program 312.

Several subsystems use the event system: the device, the scheduling system, the data management system, the display system, the settings management system, the input system, and the external communications system.

The operation of the event system is shown in the flow diagrams of FIGS. 4a, 4b, 4c, 4d, 4e, 4f, 4g, 4h, 4i, and 4j. The event system is initialized at the beginning of the program (FIG. 4a). The evenInit function 400 allocates the event queue and readies the event system for use. Deinitialization is done at the end of the program with the eventExit function 410 (FIG. 4b). The program can call the eventPost function 420 (FIG. 4c) to add an event to the queue at a certain priority. The eventGet function 430 (FIG. 4d) is called by the programs main loop to retrieve the next event and, when one is available, the eventDispatch function 440 (FIG. 4e) is called to execute the event. When no events are available, the eventGenerate function 450 (FIG. 4f) is called to generate any events that need to be generated, for example: GENERATE STATE EVENT 460 (FIG. 4g) which checks for message time out and whether the next scheduled event is due; GENERATE DATA EVENT 470 (FIG. 4h) which polls the DevSOMs; GENERATE TIME EVENT 480 (FIG. 4i) which provides a timer function; or GENERATE BUTTON EVENT 490 (FIG. 4j) which checks whether a button was pushed.

Figures 5A, 5B:
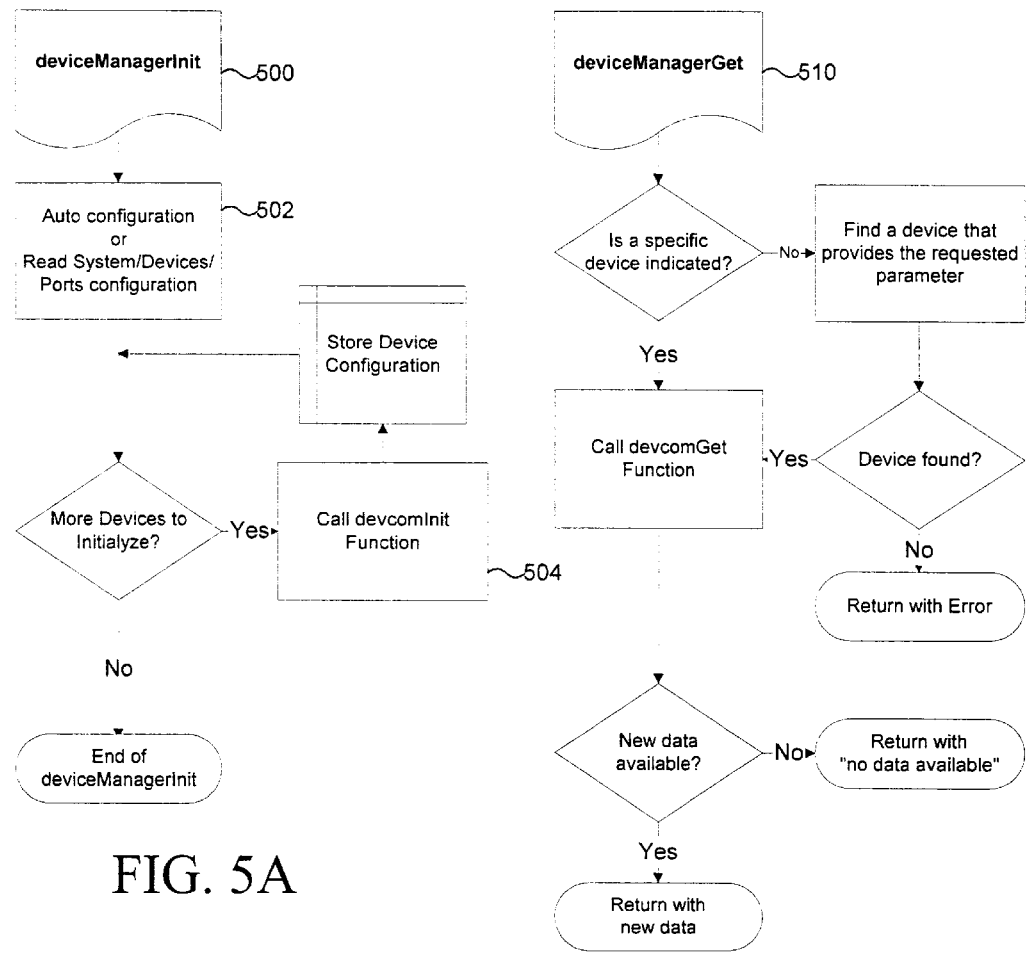
FIGS. 5a, 5b, and 5c are software flow diagrams of the functions and operation of the device management system initialization, get device, and set device routines, respectively, of the present invention.
Figure 5C:
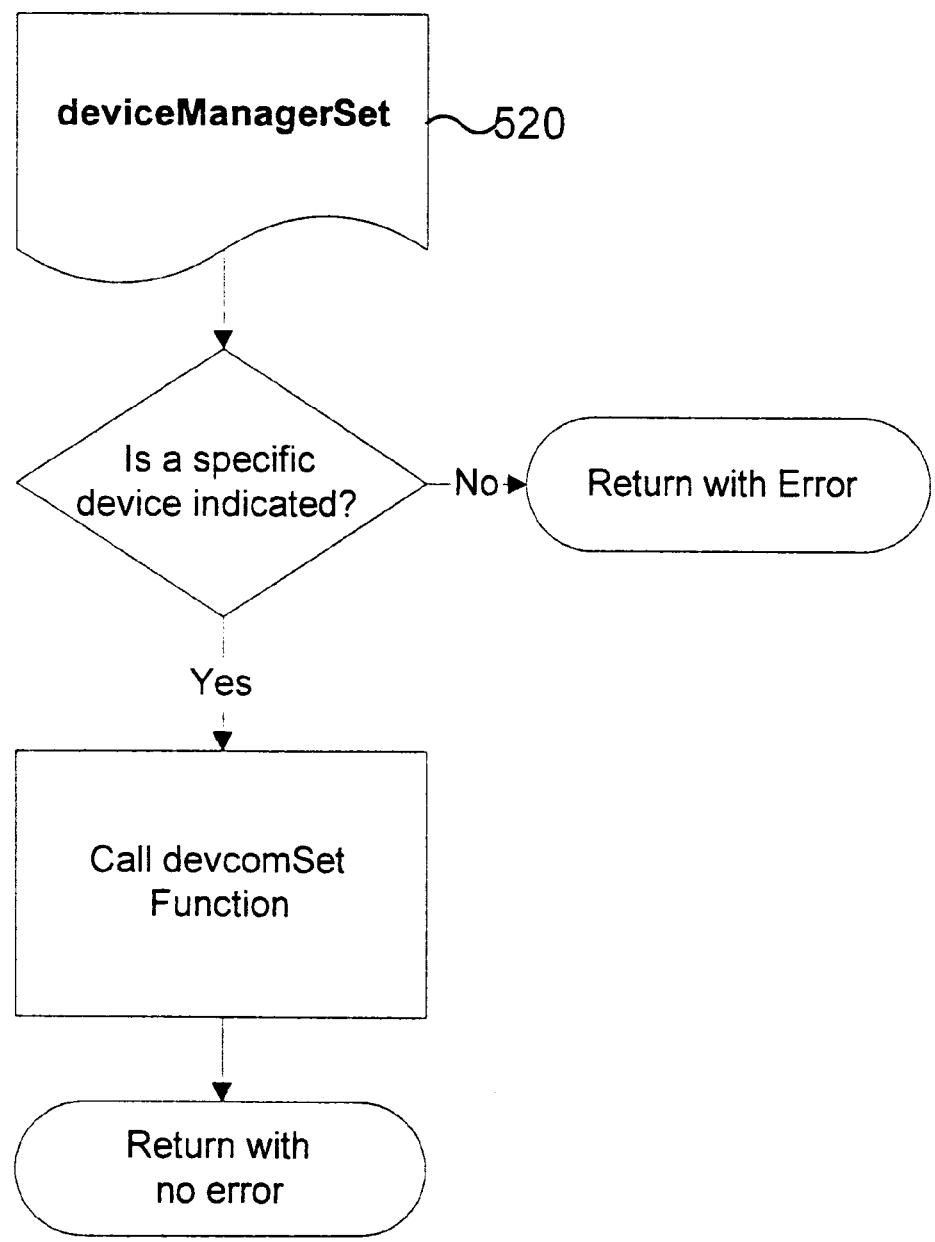
Figures 6A, 6B, 6C:
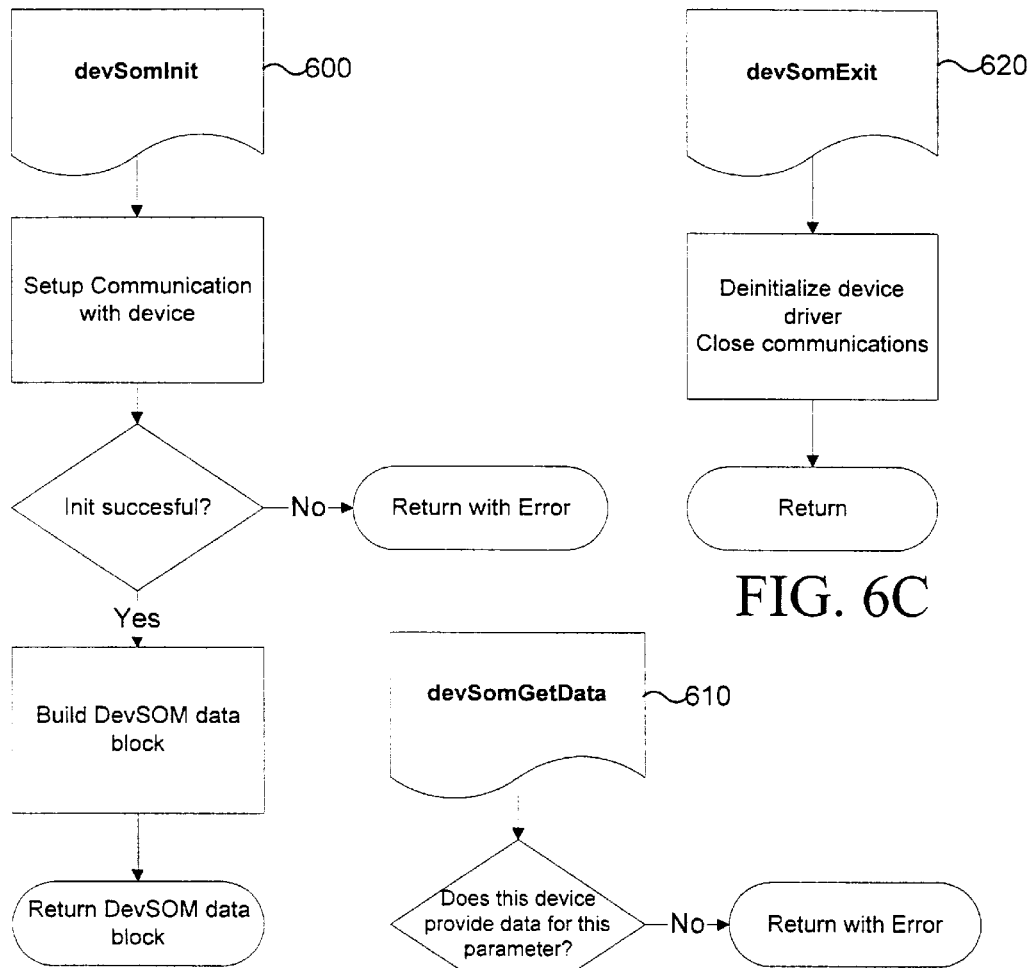
FIGS. 6a, 6b, 6c, 6d, and 6e are software flow diagrams of the functions and operation of the device communication system initialization, get data, exit, set data, poll routines, respectively, of the present invention.
Figure 6D:
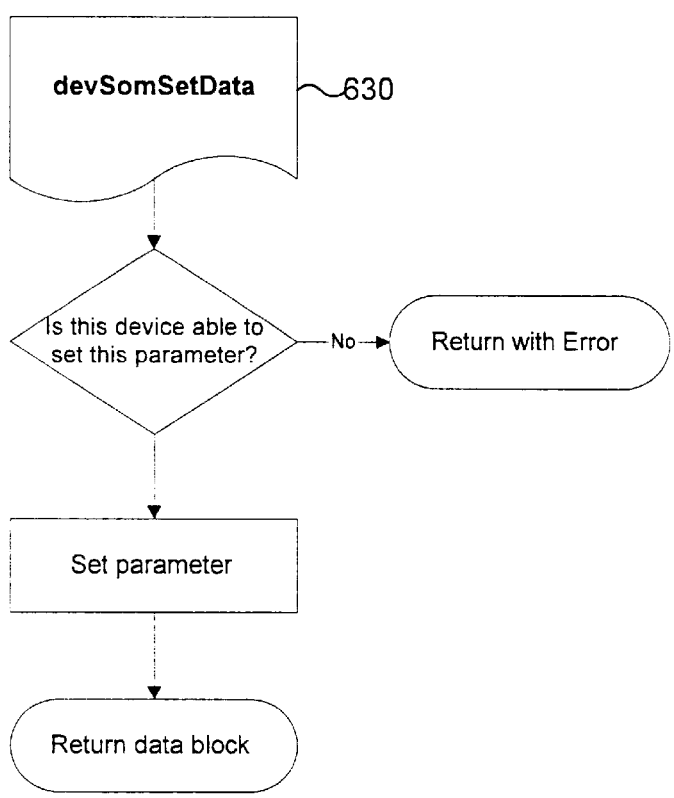
Figure 6E:
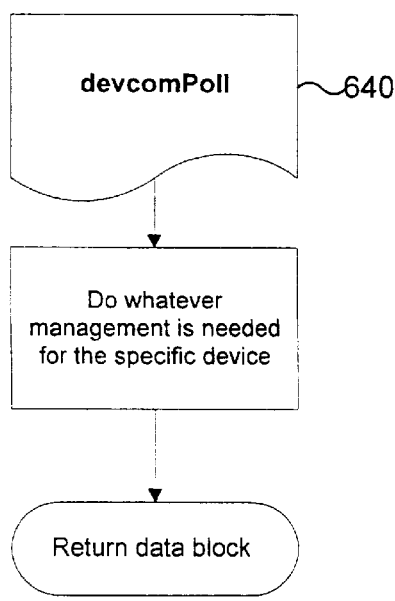

The device management system is shown in FIGS. 5a through 5c. The device manager maintains the connection with the physiologic monitors and therapeutic devices. The deviceManagerInit function 500 (FIG. 5a) is called at the start of the program. The present invention defines a Device Specific Operation Module (DevSOM) for each device containing the methods that are specific to a monitor or therapeutic device and saves the various DevSOMs in a database. This database may be updated manually or automatically by remote communication as new devices are developed and/or employed. The deviceManagerInit function 500 makes a catalog of available device DevSOMs.

Of course, each device must be identified and configured. The present invention provides a unique automatic configuration process as described herein. The preferred method is to have a database that contains: the name of the DevSOM, the name of the device, the baud rate, a request string, a response string. This database is used to identify which devices are attached to which ports as follows: For the first device in the database, the proper baud rate is set on the first port, and the first request string is sent. A fixed time is used to wait for a response. If the response matches the response string for the first device, the device is detected. If the device was not detected, the information from the second device in the database is used, until there are no more devices. This process is repeated for all the ports.

In an alternate embodiment of automatic configuration, the invention defines a database of DevSOMs that contains: the name of the DevSOM, the name of the device, response to string1 at several standard baud rates, response to string2 at several standard baud rates. This database is used to identify which devices are attached to which ports as follows: The first baud rate is selected on the first port. The first string (string1) is sent to the port. A fixed time is used to wait for a response. If the response is recognized the device is detected. If the device is not detected, a second baud rate with string1 is used. The process continues until all baud rates for string1 are tried. Then the process continues with string2. This process is repeated on the remainder of the ports. In order to rule out duplicates, it is ensured that there are no duplicate responses in the database. Other methods of polling the various ports to automatically configure the communications between the devices and the unit 10 utilizing the DevSOM database are contemplated herein.

In the preferred embodiment the DevSOMs for every device are compiled into the main program. As an alternative, the DevSOMs could be dynamically loaded from memory (or like storage medium). When automatic configuration of DevSOMs is enabled 502, the automatic configuration procedure, described above, is used. If automatic configuration is not enabled, a configuration file is read 502. Running the automatic configuration identifies which device is connected to which port and which method/protocol of a specific DevSOM is to be used. For each device the devsomInit function contained in the DevSOM for the device is called 504. As previously stated, only the specific methods/protocols are included in the DevSOM since commonalities have already been defined by the present invention.

The devsomInit function 600 of the DevSOM will do whatever initialization is needed for a specific device and will return a DevSOM data block (See Table 2) with additional information about the device. The DevSOM data block preferably contains the name of the device, the number of parameters that can be measured including their names, the number of parameters that can be modified including their names, and pointers to DevSOM functions.

TABLE 2

DevSOM Data Block

Name of the device
Number of measured parameters
Name list of measured parameters
Number of settable parameters
Name list of settable parameters
devsomExit function pointer
devsomGetData function pointer
devsomSetData function pointer
devsomPoll function pointer Currently, as shown in FIGS. 6a through 6e, the following DevSOM functions are preferably implemented in a DevSOM: devsomInit 600 (FIG. 6a)—initializes the DevSOM and returns a DevSOM data block; devsomExit 620 (FIG. 6c)—deinitializes the DevSOM; devsomGetData 610 (FIG. 6b)—retrieves the latest value of a parameter, including timestamp and units; devsomSetData 630 (FIG. 6d)—sets a device parameter; devsomPoll 640 (FIG. 6d)—give the DevSOM some CPU time to do housekeeping which some devices require.

The Device Manager (FIG. 5a–5c) is used to set and get data to/from a device. The deviceManagerGet function 510 (FIG. 5b) is called whenever data needs to be retrieved from a device. In this function, a specific device (as indicated by its port number) can be indicated, or the Device Manager can search the list of connected devices for a device that provides the indicated parameter.

To change data in a therapeutic device the deviceManagerSet function 520 (FIG. 5c) is used. It is required for this function to indicate which parameter on which device needs to be set.

Turning now to the Scheduling System (SS) of FIGS. 7a through 7d, this system is responsible for maintaining the schedule at which measurements are to be taken or at which treatment is to be modified. The schedule is maintained in a table which may be stored in memory such as stored on a Storage Medium (SM), e.g., solid state disk drive 24. Each table entry contains the starting date and time of the event, the interval at which the event is to take place, the ending date and time of the event. In addition, a daily start and stop time can be indicated if, for example, measurements are only to be taken between 8:00 a.m. and 8:00 p.m.

When an event is due the event will be posted to the Event System, which implement its execution.

Figure 7A:
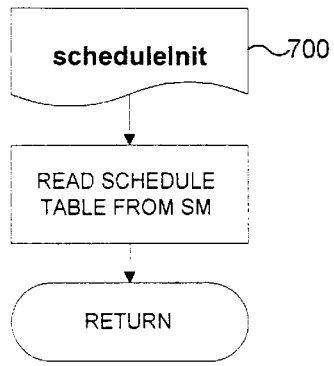
FIGS. 7a, 7b, 7c, and 7d are software flow diagrams of the functions and operation of the scheduling system initialization, check, add entry, and delete entry routines, respectively, of the present invention.
Figure 7B:
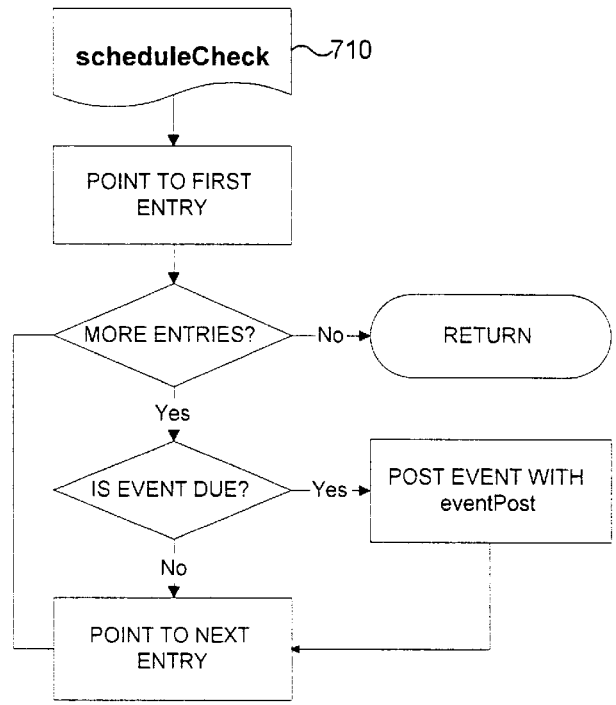
Figure 7C:
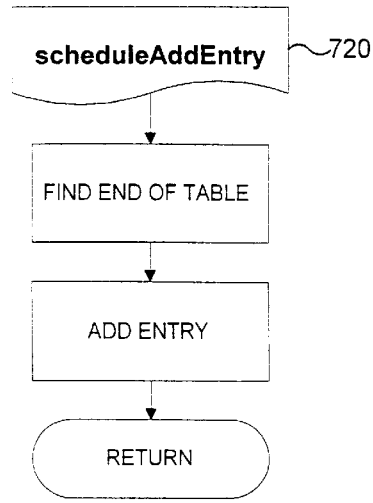
Figure 7D:
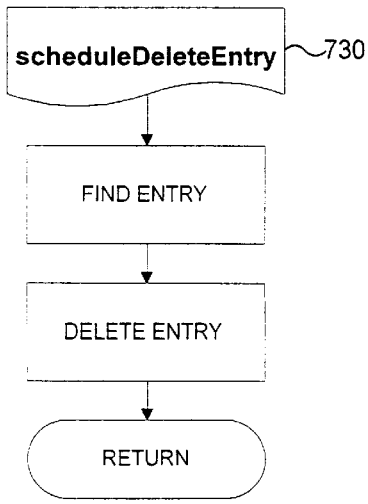

The SS is initialized at the start of the program with the scheduleInit function 700 (FIG. 7a). This function reads the schedule table from the SM. The function scheduleCheck 710 (FIG. 7b) is called often (as often as CPU power allows). This function checks the schedule and posts any events that are due. Entries can be added to the schedule table with the scheduleAddEntry function 720 (FIG. 7c), and can be deleted from the table with the scheduleDeleteEntry function 730 (FIG. 7d).

Figure 12C:
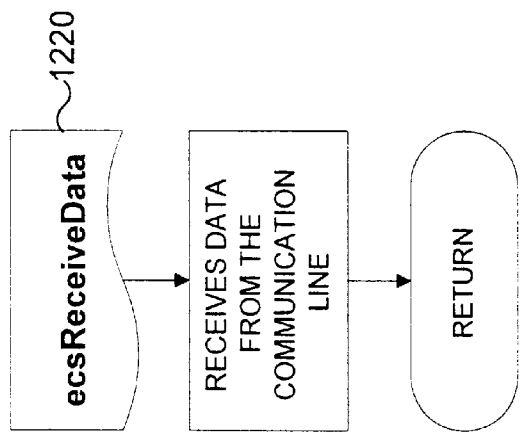
FIGS. 12a, 12b, and 12c are software flow diagrams of the functions and operation of the external communication system initialization, send data, and receive data routines, respectively, of the present invention.
Figure 12B:
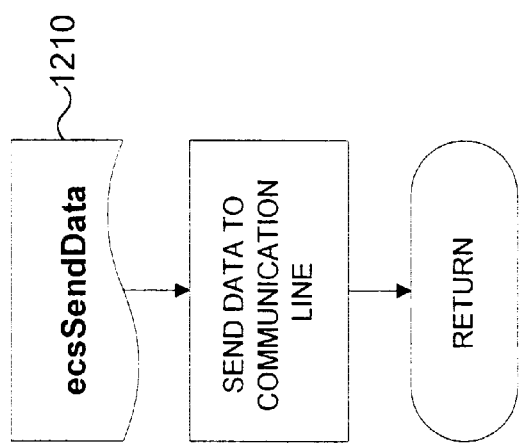
Figure 12A:
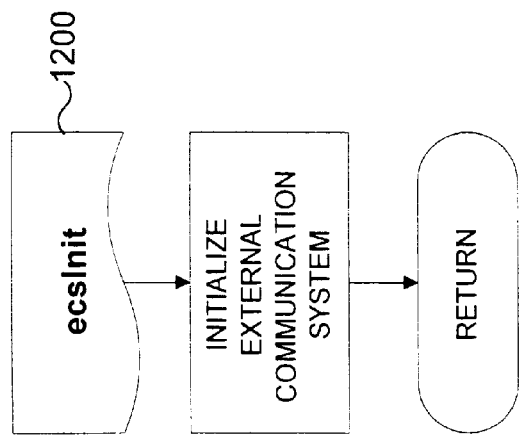

Turning now to the Data Management System (DMS) of FIGS. 8a through 8d, the DMS is responsible for storing and retrieving measured data. When data has been measured, it is passed to the DMS where it is stored in temporary storage (TS), e.g., solid state disk or RAM. Data can be retrieved from the TS and passed on to other systems via the External Communication System (FIG. 12a–12c). After data has been forwarded to another system, data can be deleted from the TS. The TS retains its data even when the power goes out.

Figure 8A:
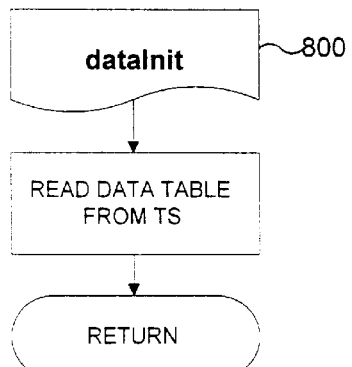
FIGS. 8a, 8b, 8c, and 8d are software flow diagrams of the functions and operation of the data management system initialization, get data, put data, and delete data routines, respectively, of the present invention.
Figure 8B:
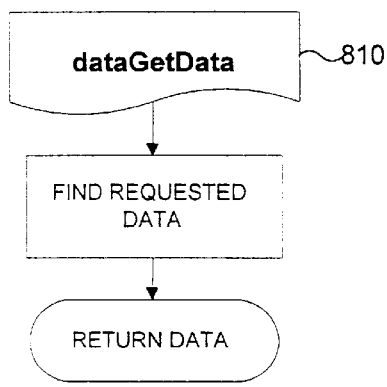
Figure 8C:
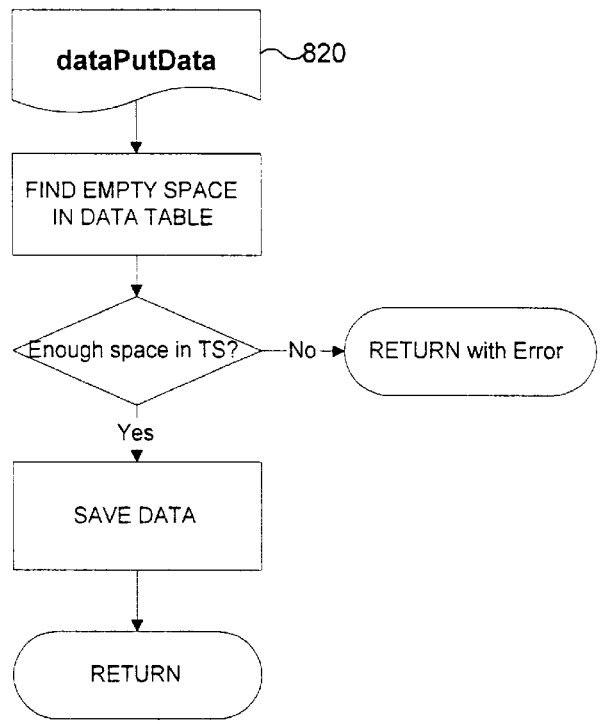
Figure 8D:
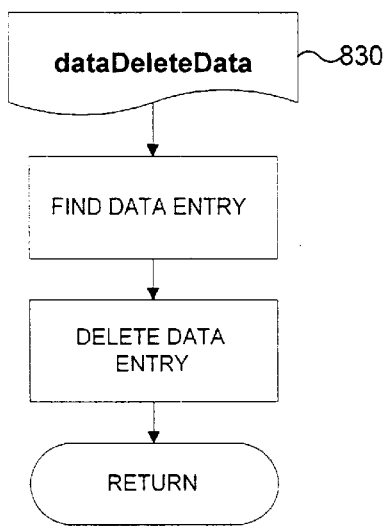

The DMS is initialized at the beginning of the program with the dataInit function 800 (FIG. 8a). This function reads the TS and creates a catalog of it in memory. The dataPutData function 820 (FIG. 8*c*) adds data to the TS and the dataDeleteData 830 (FIG. 8*d*) is used to delete data from the TS. The dataGetData function 810 (FIG. 8*b*) is used to retrieve the whole data table, or just a portion of it (for example filtered by parameter identification).

Figure 9A:
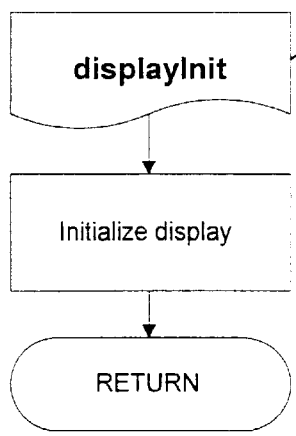
FIGS. 9a, 9b, and 9c are software flow diagrams of the functions and operation of the display system initialization, write, and display message routines, respectively, of the present invention.
Figure 9B:
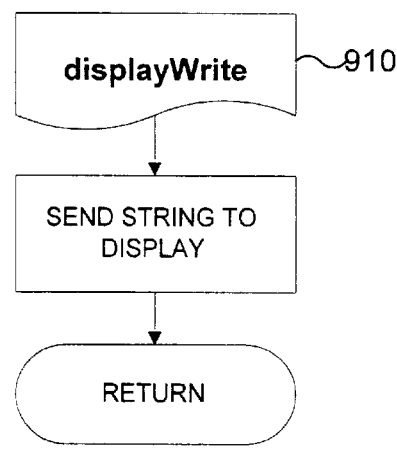
Figure 9C:
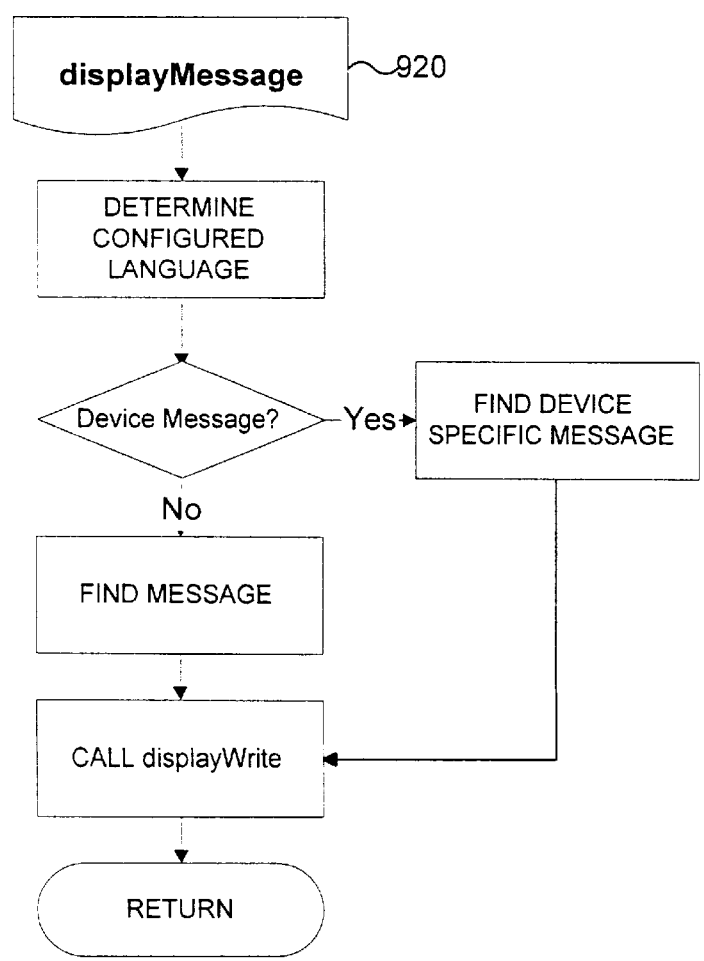

The display system (FIG. 9*a*–9*c*) is used to display short messages to the user. The displayInit function 900 (FIG. 9*a*) initializes the Display System. Messages can either be written directly to the display with the display Write function 910 (FIG. 9*b*), or predefined messages can be displayed with the displayMessage function 920 (FIG. 9*c*). The displayMessage function 920 displays the message in the configured language and can be tailored to a specific device.

Figure 10A:
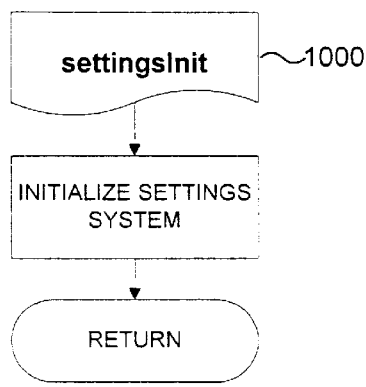
FIGS. 10a, 10b, and 10c are software flow diagrams of the functions and operation of the settings management initialization, get, and set routines, respectively, of the present invention.
Figure 10B:
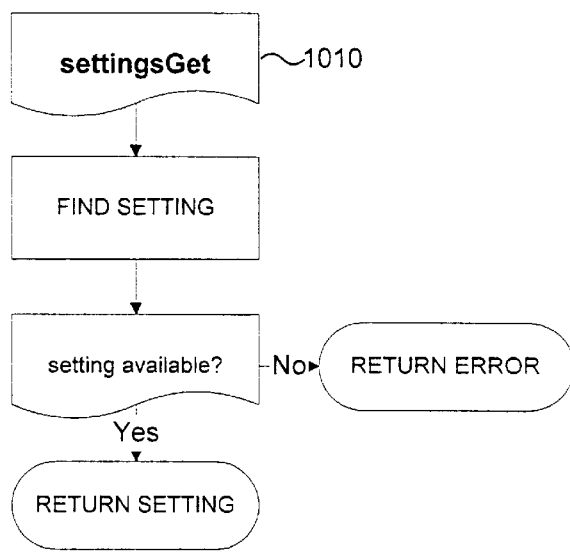
Figure 10C:
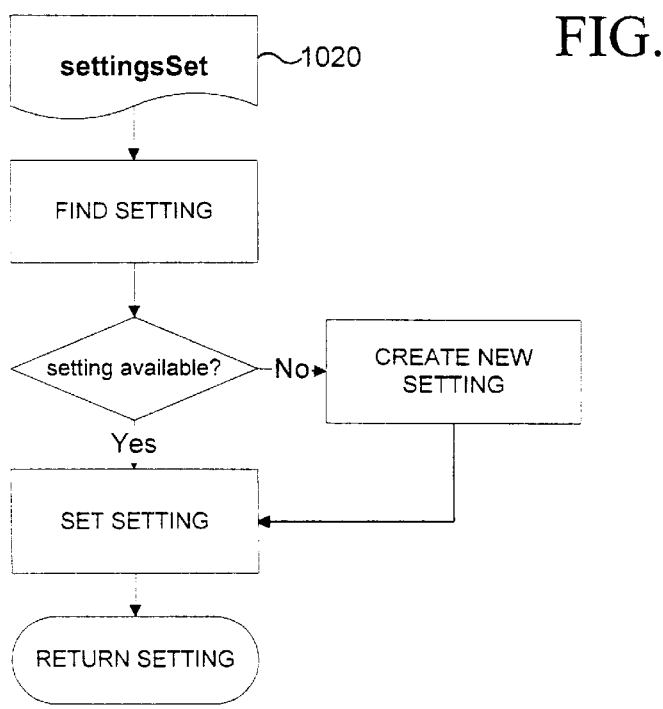

Settings Management is shown in FIGS. 10*a* through 10*c*. Settings can be stored and are retained even when power goes out. Settings include, but are not limited to: the number of patients using the device, their names, the phone number used by the external communication system, configured language, and the like. The settingsInit function 1000 (FIG. 10*a*) initializes the Settings Management system. Settings can be read with the settingsGet function 1010 (FIG. 10*b*) and set with the settingsSet function 1020 (FIG. 10*c*).

Figure 11B:
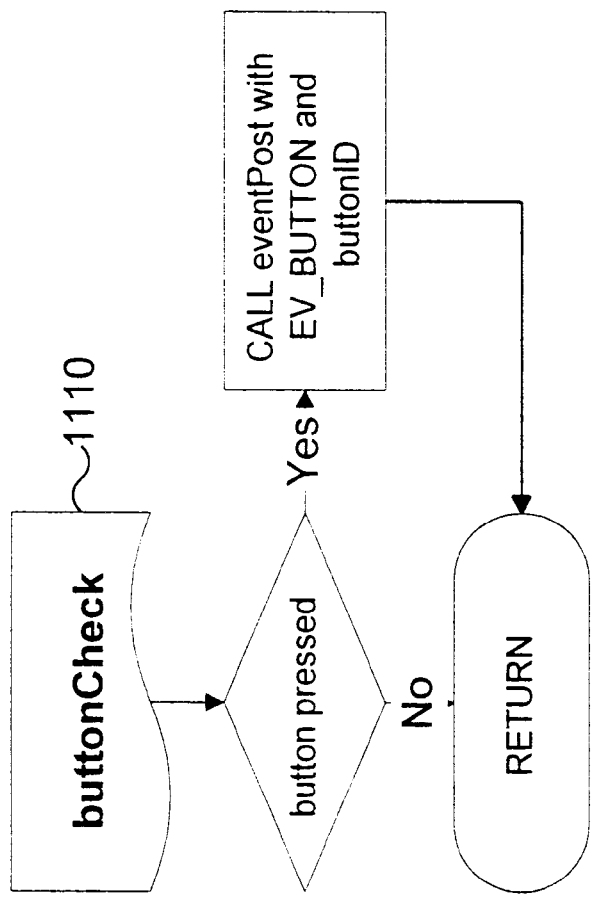
FIGS. 11a and 11b are software flow diagrams of the functions and operation of the input system initialization button and check button routines, respectively, of the present invention.
Figure 11A:
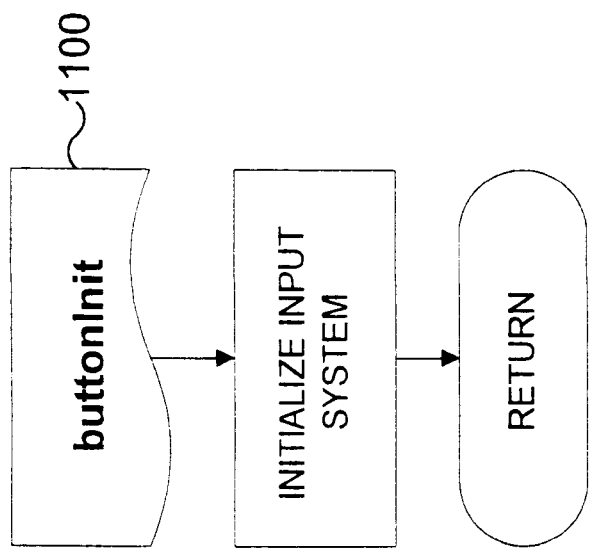

The Input System (FIG. 11*a*–11*b*) provides means for the user to interact with the system. Currently, three simple input buttons are provided in the preferred embodiment. The labels for the buttons can be changed depending on the message on the display system. The activation of a button is checked with the buttonCheck function 1110 (FIG. 11*b*) which is called from the eventGenerate function 1100 (FIG. 11*a*).

The External Communication System (FIG. 12*a*–12*c*) provides the means for transporting the data that was stored in the unit 10 to another system, or for another system to provide settings to the unit 10 or one of its attached devices. The External Communication System can communicate over standard RS-232 serial ports, modems, network adapters, or the like. Multiple connections can be maintained at the same time.

The External Communication System is initialized with the ecsInit function 1200 (FIG. 12*a*). The ecsSendData function 1210 (FIG. 12*b*) can be used to send data on the communication line and the ecsReceiveData function 1220 (FIG. 12*c*) can be used to receive data from the communication line.

Alarms can be provided for failures in the system, including an autoconfiguration failure.

Following are examples which illustrate procedures for practicing the invention. These examples should not be construed as limiting.

EXAMPLE 1

Blood Pressure Monitor

The deviceManagerInit function is called at the start of the program. The invention includes in its database a Device Specific Operation Module (DevSOM) for the particular device containing the methods that are specific to it. In this example, the invention defined the DevSOM for the "Critikon Dinamap 1846SX non-invasive blood pressure monitor with SpO2 module" by separating out the common parameters (RS-232 hardware, line printer protocol, and data set) and identifying and setting the specific protocols used in this device. The device is automatically configured according to the methods of the present invention.

In this particular example, the device utilized the common RS-232 hardware protocol. The parameters and settings for the RS-232 were defined as follows: baud rate=600, data bits=8, stop bits=1 and parity=even. The devsomInit function opens the RS-232 port with the above settings. This function will return a DevSOM data block with additional information about the device. The devsomExit function is used to close the RS-232 port.

The data for such a monitor includes the following: systolic blood pressure (BPsys), diastolic blood pressure (BPdia), heart rate (HR), and SpO2. The communication protocol was defined as "line printer" for which the common parameters of end of line (EOL) character and data formats were determined to have the following specific settings: EOL=carriage return; BPsys data format=3 ASCII characters starting at position 23 if line begins with BBC; BPdia data format=3 ASCII characters starting at position 27 if line begins with BBC; HR data format=3 ASCII characters starting at position 20 if line begins with BBC; SpO2 data format=3 ASCII characters starting at position 11 if line begins with EAA. In operation, the devsompoll function sends request data string1 (B*C<carriage return>) every even second and sends request data string2 (E*A<carriage return>) every odd second. The data is read from the device. If EOL is received, the data is parsed according to the defined data formats and stored in an internal data table ready to be retrieved by devsomGetData function. The devsomSetData function is not used with this device.

EXAMPLE 2

Multi-parameter Monitor

The deviceManagerInit function is called at the start of the program. The invention includes in its database a Device Specific Operation Module (DevSOM) for the particular device containing the methods that are specific to it. In this example, the invention defined the DevSOM for the "Propaq Encore multi-parameter monitor" by separating out the common parameters (hardware=RS-232, software=packetized format, and data set) and identifying and setting the specific parameters used in this device. The device is automatically configured according to the methods of the present invention.

In this particular example, the device utilized the common RS-232 hardware protocol. The parameters and settings for the RS-232 were defined as follows: baud rate=19200, data bits=8, stop bits=1 and parity=even. The devsomInit function opens the RS-232 port with the above settings. This function will return a DevSOM data block with additional information about the device. The devsomExit function is used to close the RS-232 port.

The data for such a monitor includes the following: systolic blood pressure (Bpsys), diastolic blood pressure (Bpdia), heart rate (HR), SpO2 and more parameters depending on connected inputs. The communication protocol was defined as "packet format" for which the common parameters of packet header (data length 2 bytes), data section (packet type, n bytes), end of packet information (CRC field—2 bytes) were determined to have the specific settings as noted in parentheses.

In operation, the devsomPoll function sends a sensor request packet (packet type 17) for each parameter to be monitored every second. It then sends an autolink packet (packet type 5) to inform the monitor that the connection is still ongoing. It also parses the response packets and fills out an internal data table. The devsomSetData function is not used with this device.

EXAMPLE 3

Infusion Pump

The deviceManagerInit function is called at the start of the program. The invention includes in its database a Device Specific Operation Module (DevSOM) for the particular device containing the methods that are specific to it. In this example, the invention defined the DevSOM for the "Alaris P6000 syringe pump" by separating out the common parameters (hardware=RS-232, software=packetized format, and data set), and identifying and setting the specific parameters used in this device. The device is automatically configured according to the methods of the present invention.

In this particular example,the device utilizes the common RS-232 hardware protocol. The parameters and settings for the RS-232 were defined as follows: baud rate=9600 baud, data bits=8, stop bits=1, and parity=none. The devsomInit function opens the RS-232 port with the above settings. This function will return a DevSOM data block with additional information about the device. The devsomExit function is used to close the RS-232 port.

The data for such a treatment device that can be retrieved include: total infused volume, selected drug, etc. The data for this device that can be set include: infusion rate, upper limit of the infused volume, etc.

The communication protocol was defined as "packet format", for which the common parameters of packet header (data length 3 bytes), data section (data length 2 bytes, data n bytes), end of packet information (CRC field 2 bytes) were determined to have the specific settings as noted in parentheses.

In operation,the devSOMPoll function sends an infused volume requestpacket ("0,VI ?") to request an update on the total infused volume, and a selected drug request packet ("0,DR ?") to request an update on the selected drug. The requested data is then sent back from the device, is parsed, and stored in an internal data table. The devSOMSetData function can be used to update the infusion rate. The devSOMSetData function will send the set rate packet ("0,RS=xxx.xml/h"), which will cause the infusion rate on the pump to change as instructed.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A system for monitoring of at least one physiologic condition of at least one patient comprising:
    (a) means for configuring a protocol of communication between at least one medical device and a data acquisition unit connected to at least one of said devices by identifying specific protocols for each connected device and automatically configuring settings for said common parameters associated with each of said protocols;
    (b) means for monitoring a patient's physiologic condition through at least one connected medical device to provide data representative of said physiologic condition;
    (c) means for communicating said data to said data acquisition unit connected to said device.

2. The system of claim 1, further comprising means for storing said data in said data acquisition unit and means for transmitting said parameter to a remote location.

3. The system of claim 1, wherein at least one of said medical devices is a monitoring device.

4. The system of claim 1, wherein at least one of said medical devices is a therapeutic device.

5. The system of claim 4, further comprising means for communicating a command to control said therapeutic device through said data acquisition unit.

6. The system of claim 5, wherein said means for communicating initiates the communication at a location remote from said data acquisition unit.

7. The system of claim 1, wherein said means for automatically configuring said specific parameter settings comprises:
    (a) means for polling each connected device,
    (b) means for comparing response from said polling step to a list of specific responses for each device; and
    (c) means for setting said specific parameter settings for each device based on said comparison.

8. A method for monitoring of at least one physiologic condition of at least one patient comprising the steps of
    (a) configuring a protocol of communication between at least one medical device and a data acquisition unit connected to at least one of said devices by identifying specific protocols for each connected device and automatically configuring settings for said common parameters associated with each of said protocols;
    (b) monitoring a patient's physiologic condition through at least one connected medical device to provide data representative of said physiologic condition;
    (c) communicating said data to said data acquisition unit connected to said device.

9. The method of claim 8, further comprising the step of storing said data in said data acquisition unit and transmitting said parameter to a remote location.

10. The method of claim 8, wherein at least one of said medical devices is a monitoring device.

11. The method of claim 8, wherein at least one of said medical devices is a therapeutic device.

12. The method of claim 11, further comprising the step of communicating a command to control said therapeutic device through said data acquisition unit.

13. The method of claim 12, wherein said communicating is initiated at a location remote from said data acquisition unit.

14. The method of claim 8, wherein said settings are automatically configured for each device by
    (a) polling each connected device,
    (b) comparing response from said polling step to a list of specific responses for each device,
    (c) setting said specific parameter set tings for each device based on said comparison.

15. A method of communicating with various devices comprising identifying specific protocols for each connected device and automatically configuring settings for common parameters associated with each of said protocols, wherein said settings are automatically configured for each device by
    (a) polling each connected device,
    (b) comparing response from said polling step to a list of specific responses for each device, and
    (c) setting said specific parameter settings for each device based upon said comparison.

16. The method of claim 15, wherein said protocols comprise hardware and software protocols for communication.

17. The method of claim 16, wherein said hardware protocols comprise RS232 type comprising common parameters of baud rate, data bits, stop bits and parity associated therewith.

18. The method of claim 16, wherein said software protocols comprise
    line printer type comprising common parameters of end of line character and line format, and packetized data type comprising common parameters of packet format, header, data format, and end of packet information.

19. The method of claim 16, wherein said protocols further comprise input/output format for data sets.

20. A method of communicating with various devices comprising identifying specific protocols for each connected device and automatically configuring settings for common parameters associated with each of said protocols, wherein said settings are automatically configured for each device by
   (a) sending a specific request string on a port for a device from a list of devices each having unique request and response strings,
   (b) receiving a specific response; and
   (c) if said response to said request string matches, thereby identifying a device, configuring settings for said common parameters associated with said specific protocols for the device on said port, otherwise repeat steps a through c for next device in said list.

21. The method of claim 20, wherein a proper baud rate is set for said device prior to sending said request string.

22. The method of claim 21, wherein said steps are repeated for each port.

23. The method of claim 20, wherein said protocols comprise hardware and software protocols for communication.

24. The method of claim 23, wherein said hardware protocols comprise RS232 type comprising common parameters of baud rate, data bits, stop bits and parity associated therewith.

25. The method of claim 23, wherein said software protocols comprise
   line printer type comprising common parameters of end of line character and line format, and
   packetized data type comprising common parameters of packet format, header, data format, and end of packet information.

26. The method of claim 23, wherein said protocols further comprise input/output format for data sets.

27. A method of communicating with various devices comprising identifying specific protocols for each connected device and automatically configuring settings for common parameters associated with each of said protocols, wherein said settings are automatically configured for each device by
   (a) selecting a baud rate setting out of a list of standard baud rate settings,
   (b) sending a first request string on a port, and
   (c) if a first response to said first request string is matched, thereby identifying a device, configuring settings for said common parameters associated with said specific protocols for the device which corresponds to said first response, otherwise repeat steps a through c for the next baud rate in said list of standard baud rates.

28. The method of claim 27, further comprising the steps of:
   (a) if no responses are matched in steps a through c of method 10, selecting a baud rate setting out of said list of standard baud rate settings,
   (b) sending a second request string on a port,
   (c) if a second response to said second request string is matched, thereby identifying a device, configuring settings for said common parameters associated with said specific protocols for the device which corresponds to said second response, otherwise repeat steps a through c herein for the next baud rate setting in said list of standard baud rates.

29. The method of claim 28, wherein said steps are repeated for each port.

30. The method of claim 27, wherein said steps are repeated for each port.

31. The method of claim 27, wherein said protocols comprise hardware and software protocols for communication.

32. The method of claim 31, wherein said hardware protocols comprise RS232 type comprising common parameters of baud rate, data bits, stop bits and parity associated therewith.

33. The method of claim 31, wherein said software protocols comprise
   line printer type comprising common parameters of end of line character and line format, and
   packetized data type comprising common parameters of packet format, header, data format, and end of packet information.

34. The method of claim 31, wherein said protocols further comprise input/output format for data sets.

35. A system for communicating with various devices comprising:
   a routine for identifying specific protocols for each connected device and automatically configuring settings for said common parameters associated with each of said protocols, wherein said routine performs the following steps:
   (a) polling each connected device,
   (b) comparing a response from said polling step to a list of specific responses for each device to identify a specific protocol for each connected device, and
   (c) configuring settings for said common parameters associated with said specific protocol for each device based on said comparison.

36. A system for communicating with various devices comprising:
   a routine for identifying specific protocols for each connected device and automatically configuring settings for said common parameters associated with each of said protocols, wherein said routine performs the following steps:
   (a) sending a specific request string for a device in a list of devices on a port, and
   (b) if a response to said request string is matched, thereby identifying a device, configuring settings for said common parameters associated with said specific protocols for said device connected to said port, otherwise repeat steps a and b for next device in said list.

37. A system for communicating with various devices comprising:
   a routine for identifying specific protocols for each connected device and automatically configuring settings for said common parameters associated with each of said protocols, wherein said routine performs the following steps:
   (a) selecting a baud rate setting out of a list of standard baud rate settings;
   (b) sending a first request string on a port; and
   (c) if a first response to said first request string is matched, thereby identifying a device, configuring settings for said common parameters associated with said specific protocols for the device which corresponds to said first response, otherwise repeat steps a through c for the next baud rate in said list of standard baud rates.

38. The computer system of claim 37, further performing the steps of:
   (a) if no responses are matched in steps a through c of claim 17, selecting a baud rate out of said list of standard baud rates;

(b) sending a second request string on said port;

(c) if a second response to said second request string is matched, thereby identifying a device, configuring settings for said common parameters associated with said specific protocols of the device which corresponds to said second response, otherwise repeat steps a through c herein for the next baud rate in said list of standard baud rates.

* * * * *

UNITED STATES PATENT AND TRADEMARK OFFICE
CERTIFICATE OF CORRECTION

PATENT NO. : 6,074,345
DATED : June 13, 2000
INVENTOR(S) : Johannes H. van Oostrom and Richard J. Melker It is certified that error appears in the above-identified patent and that said Letters Patent is hereby corrected as shown below:

Column 12, line 18: "devompoll" should read --devsomPoll--.

Column 13, line 27: "requestpacket" should read --request packet--.

Signed and Sealed this

First Day of May, 2001

Attest:

NICHOLAS P. GODICI

Attesting Officer     Acting Director of the United States Patent and Trademark Office